United States Patent
Howard et al.

(10) Patent No.: US 7,328,620 B2
(45) Date of Patent: Feb. 12, 2008

(54) METHODS AND SYSTEM FOR ULTRASOUND INSPECTION

(75) Inventors: Patrick Joseph Howard, Cincinnati, OH (US); Richard Eugene Klaassen, West Chester, OH (US)

(73) Assignee: General Electric Company, Schenectady, NY (US)

( * ) Notice: Subject to any disclaimer, the term of this patent is extended or adjusted under 35 U.S.C. 154(b) by 224 days.

(21) Appl. No.: 11/014,385

(22) Filed: Dec. 16, 2004

(65) Prior Publication Data

US 2006/0130587 A1    Jun. 22, 2006

(51) Int. Cl.
G01N 29/06    (2006.01)
G01N 29/40    (2006.01)

(52) U.S. Cl. ...................................... 73/602
(58) Field of Classification Search ................. 73/602
See application file for complete search history.

(56) References Cited

U.S. PATENT DOCUMENTS

| | | | |
|---|---|---|---|
| 4,881,177 | A | 11/1989 | McClean et al. |
| 5,445,029 | A | 8/1995 | Falsetti et al. |
| 5,533,383 | A | 7/1996 | Greene et al. |
| 5,618,994 | A | 4/1997 | Falsetti |
| 5,806,521 | A | 9/1998 | Morimoto et al. |
| 5,942,690 | A | 8/1999 | Shvetsky |
| 6,200,266 | B1 * | 3/2001 | Shokrollahi et al. ........ 600/438 |
| 6,532,820 | B1 * | 3/2003 | Fleming et al. ................ 73/627 |
| 6,568,254 | B2 | 5/2003 | Pross |
| 6,591,679 | B2 * | 7/2003 | Kenefick et al. ............... 73/597 |
| 6,925,882 | B1 * | 8/2005 | Fleming et al. ................ 73/632 |
| 6,948,369 | B2 * | 9/2005 | Fleming et al. ................ 73/588 |
| 7,017,414 | B2 | 3/2006 | Falsetti et al. |
| 7,093,491 | B2 | 8/2006 | Murphy et al. |
| 2001/0027348 | A1 | 10/2001 | Ferrone |
| 2003/0078498 | A1 * | 4/2003 | Lang et al. .................. 600/437 |
| 2003/0154062 | A1 | 8/2003 | Daft et al. |

OTHER PUBLICATIONS

European Search Report, EP 05257690.

* cited by examiner

Primary Examiner—Hezron Williams
Assistant Examiner—Rose M Miller
(74) Attorney, Agent, or Firm—William Scott Andes; Armstrong Teasdale LLP

(57) ABSTRACT

An ultrasound inspection system is provided. The ultrasound inspection system includes a pulse echo transducer and a processor that is operationally coupled to the transducer. The system facilitates reducing noise in an echo received from a near surface inspection area of a component. To facilitate reducing noise the processor is programmed to extract an A-scan data set from a B-scan image of the component. The processor is also programmed to locate a half-max point of a front surface echo in the A-scan data set. The processor is also programmed to locate the front surface of the component using a first zero crossing in a derivative of the A-scan data set.

7 Claims, 3 Drawing Sheets

METHODS AND SYSTEM FOR ULTRASOUND INSPECTION

BACKGROUND OF THE INVENTION

This invention relates generally to non-destructive testing and, more particularly, to ultrasound inspection of fabricated components.

Ultrasonic inspection techniques are used in many applications where non-destructive evaluation of a workpiece or component is required. One application of such ultrasonic inspection is in the inspection of gas turbine engine rotors. Such rotors are typically formed from a forging of a material with desired metallurgical properties, for example, Rene-88. In the production of aerospace rotating components, the entire volume of the finished component is required to be inspected ultrasonically. This requires that additional material be present on the forging when it is inspected before machining the finished component. This additional material is referred to as the material envelope and must be equal to or greater than the near surface resolution capability of the ultrasonic inspection process.

The capability to detect signals from near surface targets, such as flaws and/or discontinuities is a critical to quality feature of an ultrasonic inspection process. A near surface target, as used herein, refers to any target of interest positioned closely to either the front or back surface of the inspection sample. The near surface resolution of a given ultrasonic inspection process, as used herein, refers to the minimum distance from the front (or back) surface of the component to a target that produces an ultrasonic signal that meets the requirements of the inspection process.

From a component cost perspective, it is important to minimize the material envelope. Due to the high raw material costs for aerospace rotating components, even small reductions in material envelope can have a large impact on component cost. However, known systems are limited in the near surface resolution capability that would permit lessened material envelope requirements.

BRIEF DESCRIPTION OF THE INVENTION

In one embodiment, a method of fabricating a component is provided. The method includes receiving an ultrasound image of the component, selecting a subimage that includes a first surface of the component and an inspection area of the component, combining a filtered subimage with the selected subimage, and outputting the combined image to at least one of a display and an analyzer.

In another embodiment, an ultrasound inspection system is provided. The system includes a pulse echo transducer, and a processor operationally coupled to the transducer wherein the processor is programmed to reduce noise in an echo received from a near surface inspection area of a component.

In yet another embodiment, an ultrasound inspection system is provided. The system includes a pulse echo transducer, and a processor operationally coupled to the transducer wherein the processor is programmed to control said pulse echo transducer during a scan of a component, and receive a plurality of B-scan images from the scan.

DETAILED DESCRIPTION OF THE INVENTION

As used herein, the term "component" may include any component configured to be coupled with a gas turbine engine that may be coated with a wear-resistant coating, for example a turbine shroud support. A turbine shroud support is intended as exemplary only, and thus is not intended to limit in any way the definition and/or meaning of the term "component". Furthermore, although the invention is described herein in association with a gas turbine engine, and more specifically for use with a rotor for a gas turbine engine, it should be understood that the present invention is applicable to other gas turbine engine stationary components and rotatable components. Accordingly, practice of the present invention is not limited to rotors for a gas turbine engine.

Figure 1:
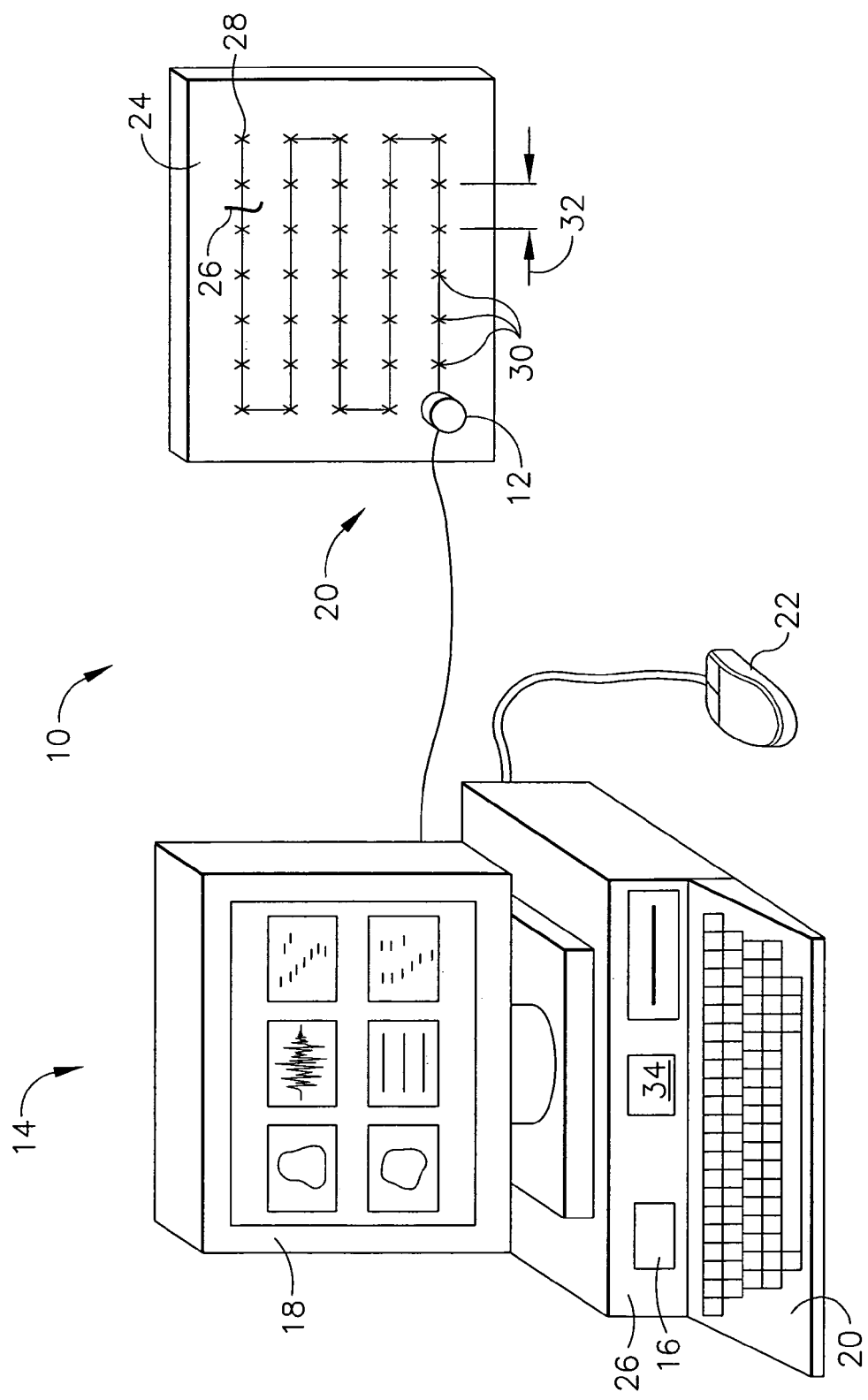
FIG. 1 is a schematic view of an exemplary embodiment of an ultrasound system.

FIG. 1 is a schematic view of an exemplary embodiment of an ultrasound system 10 that includes a pulse echo transducer 12 coupled to a control unit 14 including a processor 16, a display 18, a keyboard 20 and a mouse 22. As used herein, the term processor is not limited to just those integrated circuits referred to in the art as processors, but broadly refers to computers, processors, microcontrollers, microcomputers, programmable logic controllers, application specific integrated circuits, and other programmable circuits. Control unit 14 is configured to acquire, analyze and display ultrasonic test data. In the exemplary embodiment, ultrasound system 10 is a Pulse echo (PE) ultrasound test apparatus that uses a single transducer located on one side of the component that functions as both a transmitter and a receiver. Using pulse echo testing only requires access to one side of the test component. In various embodiments ultrasound system 10 may include an electromechanical apparatus for moving transducer 12 across the surface of the test component and the electromechanical scanning apparatus may include one or more position sensors that monitor the position of the moving transducer.

In use, transducer 12 is placed in acoustical conduct with a component 24 to be tested and ultrasound is introduced to component 24. In one embodiment, a known acoustic gel is placed between component 24 and transducer 12 to facilitate sound transfer between component 24 and transducer 12. In another embodiment, component 24 and transducer 12 are placed proximate each other submerged in a liquid that facilitates ultrasound wave travel through the liquid. In an exemplary embodiment using the liquid in an automated setting, system 10 includes a rotatable table (not shown) including at least one collet or mandrel (not shown). Component 24 is automatically chucked in the collet or onto the mandrel and the table is rotated or translated such that component 24 remains in close proximity to transducer 12 during a scan. Transducer 12 emits ultrasonic energy which is at least partially reflected when an interface 26 is encountered within component 24 (such as a discontinuity, inclusion or micro-crack) or at an interface on a far side (relative to transducer 12) of component 24 between component 24 and the liquid. When the ultrasound wave contacts the interface, a portion of the sound energy is reflected back through the component toward ultrasonic transducer 12. Ultrasonic transducer 12 may used as both a transmitter that produces RF sound wave pulses and as a receiver that records the reflected RF sound wave signals. The time between when an RF pulse is transmitted and an RF reflection is received equals the time it took for the sound wave to pass into the test component, contact the area of discontinuity, and travel back to the ultrasonic transducer 12. Thus, the time between transmission and reception is related to the depth of the discontinuity. The amplitude of the RF signal is related to the magnitude of the discontinuity, as the larger the discontinuity, the more sound energy is reflected back towards the ultrasonic transducer 12. In one embodiment, ultrasonic transducer 12 is located on a mechanical arm (not shown) whose movement is precisely controlled by control unit 14. The mechanical arm moves the ultrasonic transducer 12 over the surface of test component 24 in a precisely controlled scan during testing. The mechanical arm moves the ultrasonic transducer 12 from a starting point 28. As ultrasonic transducer 12 moves across test component 24, ultrasonic test data is taken at preprogrammed data points 30. In the exemplary embodiment, data points 30 are equally spaced apart a distance 32. In an alternative embodiment, control unit 14 is programmed to take data at irregular distances. Position sensors (not shown) may be used to facilitate determining a position of ultrasonic transducer 12 during a scan. The position data may then be used to reconstruct test component 24 in ultrasound images.

As ultrasonic transducer 12 receives the reflected sound waves at an individual data point 30, the information is passed to control unit 14 in the form of an RF signal. This RF signal is digitized by control unit 14 and the resulting digitized data is passed to and stored as a data array in a memory 34 within control unit 14. The location on test component 24 from which each set of digitized data originated can be determined by knowing the scan pattern and by knowing the position of the digitized data in the data array.

Figure 2:
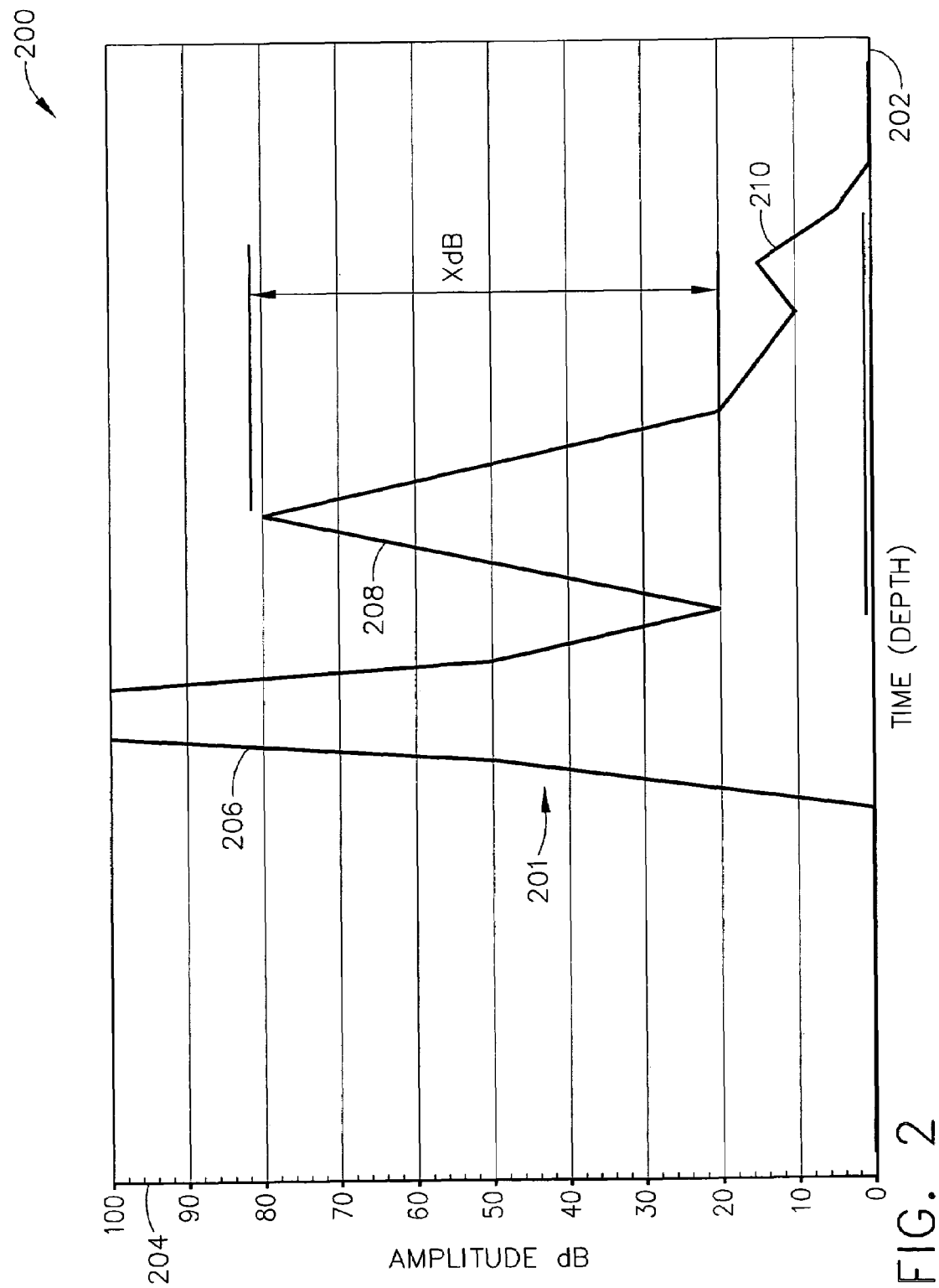
FIG. 2 is a graph of an exemplary A-scan waveform of a component, such as the component shown in FIG. 1.

FIG. 2 is a graph 200 of an exemplary A-scan waveform 201 of a component, such as component 24 (shown in FIG. 1). The digitized RF signal may be displayed as an A-Scan graph of the reflected RF sound energy signal received by ultrasonic transducer 12 wherein time is plotted, for example along an X-axis 202 and amplitude may be plotted along a Y-axis 204. As described above, the greater the relative size of interface 26 in test component 24 the greater the amplitude of sound energy reflected, thus the greater the amplitude of the RF signal. A front surface echo 206 or first reflection has amplitude that is caused by the front surface of test component 24. A second and third smaller amplitude reflection 208 and 210 are caused by a reference fault purposefully introduced into component 24 or a discontinuity in an inspection gate area of component 24. Reflections 208, and 210 may be voids, delaminations, or other flaws within the test component, or in a component that is made of composite layers, could be the intersections between individual composite layers forming the composite component.

A near surface resolution of ultrasonic inspection system 10 may generally be controlled by ultrasonic transducer 12, the control unit 14 used to transmit and receive the ultrasound from transducer 12, and the signal-to-noise ratio (SNR) required for near surface targets by the inspection procedure. The resolution is typically defined as the difference in amplitude (measured in dB) separating the peak amplitude of the target from the minimum signal amplitude between that peak and the peak amplitude of the front surface signal. The inspection area (or inspection gate) is then set based on the near surface target that produces the amount of dB required by the inspection procedure for near surface resolution. Ultrasound system 10 records an entire ultrasound waveform and stores it for later access. The waveform data can be recorded either for just the inspection area, or a larger area which can include the front and/or back surface reflections. Once the ultrasonic waveform data has been recorded, it is available for post-processing using signal and image processing techniques.

Figure 3:
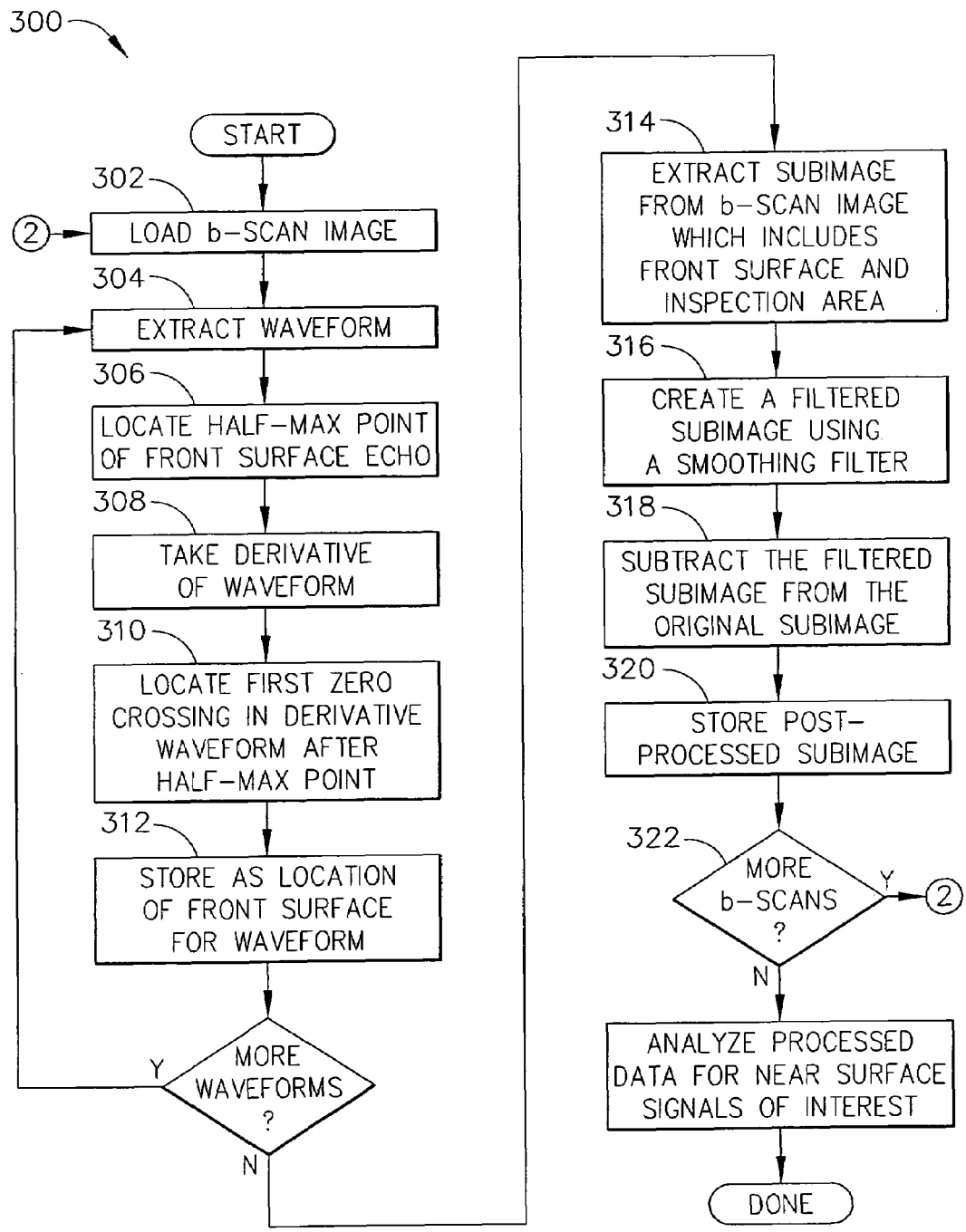
FIG. 3 is a flow chart of an exemplary method for improving near surface resolution of an ultrasound system, such as the ultrasound system shown in FIG. 1.

FIG. 3 is a flow chart of an exemplary method 300 for improving near surface resolution of an ultrasound system, such as ultrasound system 10 (shown in FIG. 1). Method 300 facilitates improving near surface resolution by collecting ultrasonic waveform data for the inspection area plus the surface echoes. The algorithm that implements the steps of method 300 may be embodied in a software code segment that is stored in a memory of control unit 14. The waveform data may be collected over a two-dimensional grid of points on component 24 during an inspection. The waveform data from the area around the surface signals are post-processed using signal and image processing techniques. The result is an improved near surface resolution when compared to the gated maximum amplitude approach. The resulting data can the be further processed for the detection of signals of interest in the inspection either by an automated detection algorithm or by manual review. One of a plurality of B-scan images is loaded 302 into a memory of ultrasound inspection system 10. In the exemplary embodiment, ultrasound inspection system 10 collects a three-dimensional set of data for processing, for example, two spatial dimensions on the surface of the inspection specimen and time in the direction of propagation of the ultrasonic signal. A two-dimensional image in one spatial dimension and time extracted from the 3D data set may be referred to as a B-scan.

For each B-scan image, an A-scan waveform is extracted 304. A position in time of front surface echo 206 for each spatial location is located by processing each waveform (time signal from a single spatial location) individually. The maximum value of the waveform may correspond to the maximum value of the front surface signal. Due to the digitized nature of the front surface waveform, using this maximum value may not consistently define the front surface. Rather, the algorithm uses the maximum value to locate 306 the first time point $t_h$ that has an amplitude greater than the half-max value. A numerical derivative of the waveform is taken 308. The first time point $t_f$ in the derivative that is greater than $t_h$ and where the value of the derivative is less than zero is located 310. Point $t_f$ is stored 312 as the location of the front surface for that waveform. This process is repeated until the front surface location for all the waveforms in the B-scan image have been determined.

Alternatively, the front surface locations may be determined by processing b-scan image as a whole. In this method, two-dimensional edge enhancement filters such as Sobel, Robers, Gradiant, Laplacian, Kirsch, Canny, Shen-Castan, or Marr-Hildreth are applied to the image. The edge enhanced images is then post-processed to determine the set of front surface locations $t_f$.

Using the set of front surface locations $t_f$ for the B-scan image, a subimage the contains the front surface echo and the area of interest for inspection after the front surface echo is extracted 314. In the exemplary embodiment, the algorithm removes the front surface echo from the extracted subimage by, for example, applying background subtraction to create 316 a filtered subimage. After removing the front surface signal, any remaining signals will be due to near surface reflectors. To apply background subtraction, a composite background image is created by filtering the B-scan with a smoothing filter. This filter should smooth the response in the spatial dimension of the B-scan image such that any echoes from near surface targets are suppressed such that they will standout after the future image subtraction step. The filter configuration may be selectable depending on the target component properties, transducer type, and a spatial index. The filtered subimage is subtracted 318 from the extracted subimage to create a processed subimage, which may be stored 320 in a memory of control unit 14, or other memory or storage device.

Alternatively, the precise location of the front surface obtained in the points $t_f$, can be used to accurately extract signals a narrow band of time that is a fixed distance from that location without any post-processing such as the background subtraction step described above.

Method 300 may be repeated 322 for all the B-scans images in the data set. After all the B-scan images have been processed, the processed data set can be further analyzed with the advantage that the near surface targets will have a higher signal-to-noise ratio due to the image processing operations.

A technical effect of the various embodiments of the systems and methods described herein include at least one of improving the detection of near surface discontinuities in objects being scanned.

The above-described methods and apparatus are cost-effective and highly reliable for improving near surface resolution of an ultrasound inspection system. The methods and apparatus describe collecting ultrasound waveform data for an inspection area and surface echoes over a two-dimensional grid of points on the component being inspected. The waveform data from the area around the surface signals are post-processed using signal and image processing techniques. The result is an improved near surface resolution. The resulting data can the be further processed for the detection of signals of interest in the inspection either by an automated detection algorithms or by manual review. The methods and apparatus described above facilitate fabrication, assembly, and reducing the maintenance cycle time of components in a cost-effective and reliable manner.

While the invention has been described in terms of various specific embodiments, those skilled in the art will recognize that the invention can be practiced with modification within the spirit and scope of the claims.

What is claimed is:

1. An ultrasound inspection system comprising:
   a pulse echo transducer; and
   a processor operationally coupled to said transducer for reducing noise in an echo received from a near surface inspection area of a component, said processor programmed to:
   extract an A-scan data set from a B-scan image of the component;
   locate a half-max point of a front surface echo in the A-scan data set; and
   locate the front surface of the component using a first zero crossing in a derivative of the A-scan data set.

2. An ultrasound inspection system in accordance with claim 1 wherein said processor is configured to extract the A-scan data set from the B-scan image by extracting a waveform from the B-scan image.

3. An ultrasound inspection system in accordance with claim 2 wherein said processor is configured locate the half-max point of the front surface echo in the A-scan data set by locating a half-max point of a front surface echo in the waveform.

4. An ultrasound inspection system in accordance with claim 3 wherein said processor is further configured to take a derivative of the waveform.

5. An ultrasound inspection system in accordance with claim 4 wherein said processor is configured locate the front surface of the component using the first zero crossing in the derivative of the A-scan data set by locating the front surface of the component at a first zero crossing in the derivative waveform after the half-max point.

6. An ultrasound inspection system in accordance with claim 1 wherein said processor is further configured to:
   apply a two dimensional edge enhancement filter to the B-scan image to generate a filtered B-scan image; and
   extract the A-scan data set from the filtered B-scan image.

7. An ultrasound inspection system in accordance with claim 5 wherein said processor is further configured to:
   apply at least one of a Sobel filter, a Robers filter, a Gradiant filter, a Laplacian filter, a Kirsch filter, a Canny filter, a Shen-Castan filter, and a Marr-Hildreth filter to the B-scan image to generate a filtered B-scan image; and
   extract the A-scan data set from the filtered B-scan image.

* * * * *